US010463238B2

(12) United States Patent
Makita

(10) Patent No.: US 10,463,238 B2
(45) Date of Patent: Nov. 5, 2019

(54) ENDOSCOPE AND HARD MEMBER

(71) Applicant: OLYMPUS CORPORATION, Tokyo (JP)

(72) Inventor: Kenji Makita, Machida (JP)

(73) Assignee: OLYMPUS CORPORATION, Tokyo (JP)

( * ) Notice: Subject to any disclaimer, the term of this patent is extended or adjusted under 35 U.S.C. 154(b) by 45 days.

(21) Appl. No.: 15/383,747

(22) Filed: Dec. 19, 2016

(65) Prior Publication Data

US 2017/0095140 A1 Apr. 6, 2017

Related U.S. Application Data

(63) Continuation of application No. PCT/JP2015/077202, filed on Sep. 25, 2015.

(30) Foreign Application Priority Data

Jan. 30, 2015 (JP) ................................ 2015-017721

(51) Int. Cl.
*A61B 1/00* (2006.01)
*A61B 1/005* (2006.01)
(Continued)

(52) U.S. Cl.
CPC ........ *A61B 1/00172* (2013.01); *A61B 1/0008* (2013.01); *A61B 1/0011* (2013.01);
(Continued)

(58) Field of Classification Search
CPC .................................................. A61B 1/00128
(Continued)

(56) References Cited

U.S. PATENT DOCUMENTS

2009/0093679 A1* 4/2009 Suigetsu ............ G02B 23/2476 600/139
2013/0245376 A1* 9/2013 Oku .................. A61B 1/00071 600/129
2014/0018776 A1 1/2014 Takeuchi et al.

FOREIGN PATENT DOCUMENTS

JP 10-43130 A 2/1998
JP H11-056760 A 3/1999
(Continued)

OTHER PUBLICATIONS

International Search Report dated Dec. 28, 2015 received in PCT/JP2015/077202.

(Continued)

*Primary Examiner* — Alexandra L Newton
*Assistant Examiner* — Rynae Boler
(74) *Attorney, Agent, or Firm* — Scully, Scottt, Murphy & Presser, P.C.

(57) ABSTRACT

An endoscope includes an insertion section configured to be inserted into a subject to observe an inside of the subject. The insertion section includes a cylindrical connection member, and a hard member having a fitting portion fitted into the connection member and secured to the connection member with an adhesive applied on an outer surface of the fitting portion. At least one of the fitting portion and the connection member includes: a dam portion extending in an axial direction of the insertion section along the outer surface of the fitting portion to block the adhesive flowing along the outer surface of the fitting portion; and a storage portion continuously provided to the dam portion to partially store the adhesive blocked by the dam portion.

16 Claims, 11 Drawing Sheets

(51) Int. Cl.
*A61B 1/06* (2006.01)
*A61B 1/018* (2006.01)
*G02B 23/24* (2006.01)
*A61B 8/12* (2006.01)
*G02B 23/26* (2006.01)

(52) U.S. Cl.
CPC ........ *A61B 1/0051* (2013.01); *A61B 1/00165* (2013.01); *A61B 1/018* (2013.01); *A61B 1/06* (2013.01); *G02B 23/2476* (2013.01); *A61B 1/0055* (2013.01); *A61B 8/12* (2013.01); *G02B 23/26* (2013.01)

(58) Field of Classification Search
USPC .................................................. 600/127, 129
See application file for complete search history.

(56) References Cited

FOREIGN PATENT DOCUMENTS

| | | | |
|---|---|---|---|
| JP | 2009-18080 | A | 1/2009 |
| JP | 2012-235880 | A | 12/2012 |
| JP | 3183819 | U | 5/2013 |
| JP | 2014-236833 | A | 12/2014 |

OTHER PUBLICATIONS

Extended Supplementary European Search Report dated Aug. 14, 2018 in European Patent Application No. 15 88 0058.1.

* cited by examiner

ENDOSCOPE AND HARD MEMBER

CROSS REFERENCES TO RELATED APPLICATIONS

This application is a continuation of PCT international application Ser. No. PCT/JP2015/077202, filed on Sep. 25, 2015 which designates the United States, incorporated herein by reference, and which claims the benefit of priority from Japanese Patent Application No. 2015-017721, filed on Jan. 30, 2015, incorporated herein by reference.

BACKGROUND

1. Technical Field

The disclosure relates to an endoscope and a hard member.

2. Related Art

Conventionally, endoscopes have been known in which a soft and elongated insertion section is inserted into a subject such as a human to observe inside the subject (e.g., see JP 2009-18080 A).

In an endoscope described in JP 2009-18080 A, an insertion section includes a connection tube (hereinafter, referred to as connection member) being a cylindrical metal member, and a distal end portion (hereinafter, referred to as hard member) positioned on a distal end side of the insertion section relative to the connection member, and secured to the connection member. Furthermore, the hard member is secured to the connection member with screws, while partially fitted into the connection member (hereinafter, referred to as fitting portion).

SUMMARY

In some embodiments, an endoscope includes an insertion section configured to be inserted into a subject to observe an inside of the subject. The insertion section includes a cylindrical connection member, and a hard member having a fitting portion fitted into the connection member and secured to the connection member with an adhesive applied on an outer surface of the fitting portion. At least one of the fitting portion and the connection member includes: a dam portion extending in an axial direction of the insertion section along the outer surface of the fitting portion to block the adhesive flowing along the outer surface of the fitting portion; and a storage portion continuously provided to the dam portion to partially store the adhesive blocked by the dam portion.

In some embodiments, a hard member is used for an insertion section of an endoscope for observing an inside a subject, and is secured to a cylindrical connection member. The hard member includes a fitting portion fitted into the connection member and secured to the connection member with an adhesive applied on an outer surface of the fitting portion. The fitting portion includes: a housing portion extending from a leading end of the fitting portion to an inside of the fitting portion; a cut-out portion formed by cutting out part of the fitting portion from the leading end to communicate inside and outside of the housing portion with each other; a dam portion extending in an axial direction of the insertion section along the outer surface of the fitting portion to block the adhesive flowing to the cut-out portion along the outer surface of the fitting portion; and a storage portion continuously provided to the dam portion to partially store the adhesive blocked by the dam portion.

The above and other features, advantages and technical and industrial significance of this invention will be better understood by reading the following detailed description of presently preferred embodiments of the invention, when considered in connection with the accompanying drawings.

DETAILED DESCRIPTION

Modes for carrying out the present invention (hereinafter referred to as "embodiment(s)") will be described below with reference to the drawings. The present invention is not limited to the embodiments described below. The same reference signs are used to designate the same elements throughout the drawings.

First Embodiment

Outline of Configuration of Endoscope System

Figure 1:
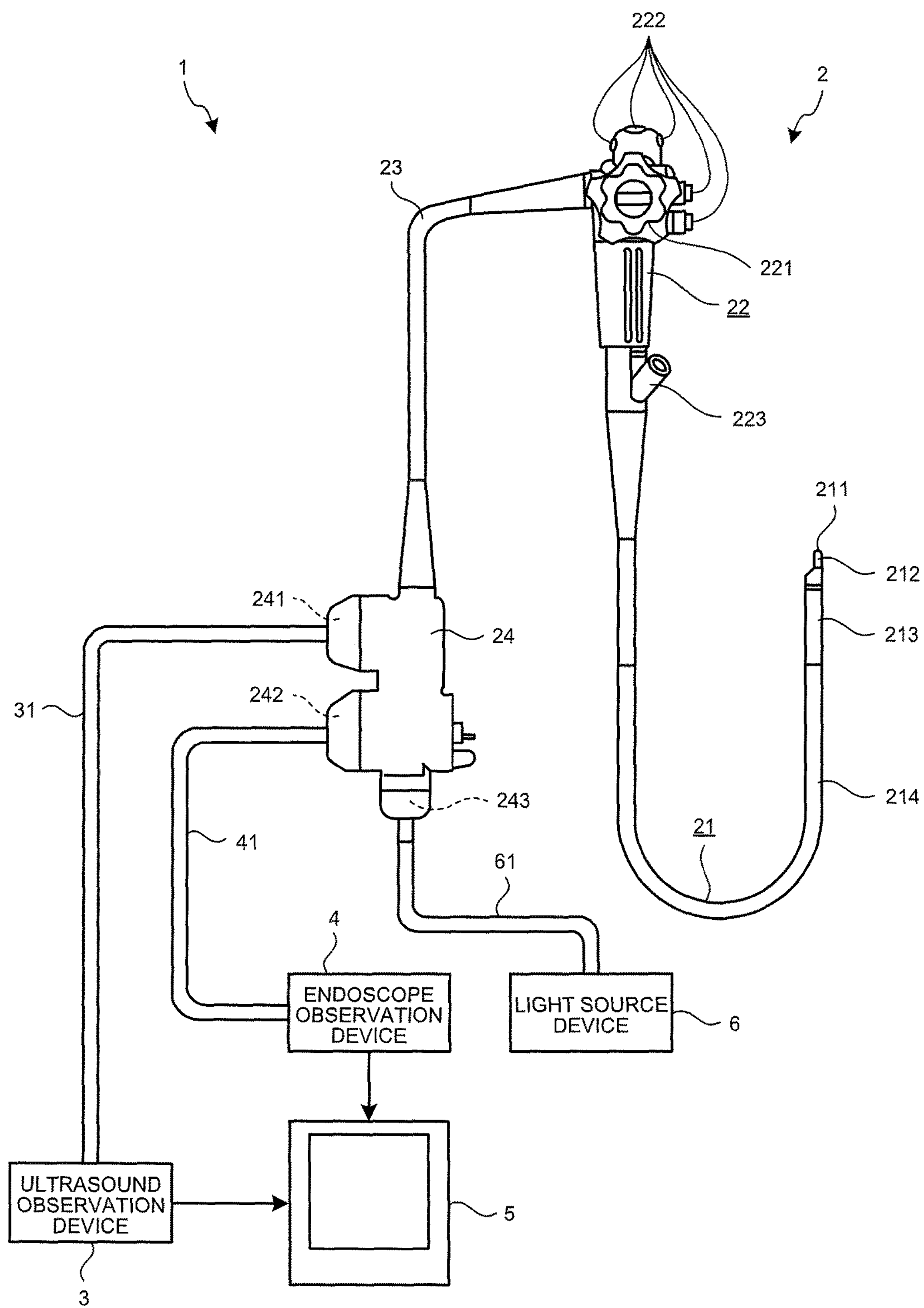
FIG. 1 is a schematic view of an endoscope system according to a first embodiment of the present invention.

FIG. 1 is a schematic view of an endoscope system 1 according to a first embodiment of the present invention.

The endoscope system 1 is a system performing ultrasonic diagnosis in a subject such as a human, using an ultrasound endoscope. As illustrated in FIG. 1, the endoscope system 1 includes an endoscope 2, an ultrasound observation device 3, an endoscope observation device 4, a display device 5, and a light source device 6.

The endoscope 2 is an ultrasound endoscope configured to be partially inserted into the subject, and having a function of transmitting ultrasound pulses toward a body wall in the subject, receiving an ultrasound echo reflected from the subject, and outputting an echo signal, and a function of imaging inside the subject and outputting an image signal.

A detailed configuration of the endoscope 2 will be described later.

The ultrasound observation device 3 is electrically connected to the endoscope 2 through an ultrasound cable 31 (FIG. 1), and outputs a pulse signal to the endoscope 2 and receives an echo signal input from the endoscope 2, through the ultrasound cable 31. Furthermore, the ultrasound observation device 3 performs predetermined processing on the echo signal to generate an ultrasound image.

The endoscope observation device 4 is electrically connected to the endoscope 2 through a video cable 41 (FIG. 1), and receives an image signal input from the endoscope 2 through the video cable 41. Furthermore, the endoscope observation device 4 performs predetermined processing on the image signal to generate an endoscopic image.

The display device 5 is configured using liquid crystal or organic electro luminescence (EL), and displays the ultrasound image generated in the ultrasound observation device 3, the endoscopic image generated in the endoscope observation device 4, or the like.

The light source device 6 is connected to the endoscope 2 through an optical fiber cable 61 (FIG. 1), and supplies illumination light illuminating inside the subject, to the endoscope 2, through the optical fiber cable 61.

Configuration of Endoscope

As illustrated in FIG. 1, the endoscope 2 includes an insertion section 21, an operating unit 22, a universal cable 23, and a connector 24.

Note that, "distal end side" described below represents a distal end side of the insertion section 21. In addition, "proximal end side" described below represents a side away from the distal end of the insertion section 21.

The insertion section 21 is a portion inserted into the subject. As illustrated in FIG. 1, the insertion section 21 includes an ultrasound probe 211 provided on the distal end side, a hard member 212 connected to the proximal end side of the ultrasound probe 211, a bending section 213 connected on the proximal end side of the hard member 212 to be bendable, and a flexible tube portion 214 connected to the proximal end side of the bending section 213.

Although not specifically illustrated, the insertion section 21 has therein a light guide for transmitting illumination light supplied from the light source device 6, a plurality of signal cables for transmitting various signals, and a treatment tool insertion passage through which a treatment tool is inserted.

A detailed configuration of the distal end side of the insertion section 21 (the ultrasound probe 211, the hard member 212, and the bending section 213) will be described later.

The operating unit 22 is a portion connected to the proximal end side of the insertion section 21, and receives various operation from a physician or the like. As illustrated in FIG. 1, the operating unit 22 includes a bending knob 221 for bendably operating the bending section 213, and a plurality of operation members 222 for performing various operations.

Furthermore, in the operating unit 22, a treatment tool insertion opening 223 is formed. The treatment tool insertion opening 223 communicates with the treatment tool insertion passage formed in the insertion section 21, and inserts a treatment tool through the treatment tool insertion passage.

The universal cable 23 is a cable extending from the operating unit 22, and the signal cables for transmitting various signals, an optical fiber for transmitting illumination light supplied from the light source device 6, and the like are disposed therein.

The connector 24 is provided at a distal end of the universal cable 23. Furthermore, the connector 24 includes first to third connector portions 241 to 243 to which the ultrasound cable 31, the video cable 41, and the optical fiber cable 61 are respectively connected.

A detailed configuration of the first and second connector portions 241 and 242 will be described later.

Configuration of Insertion Section

Figure 2:
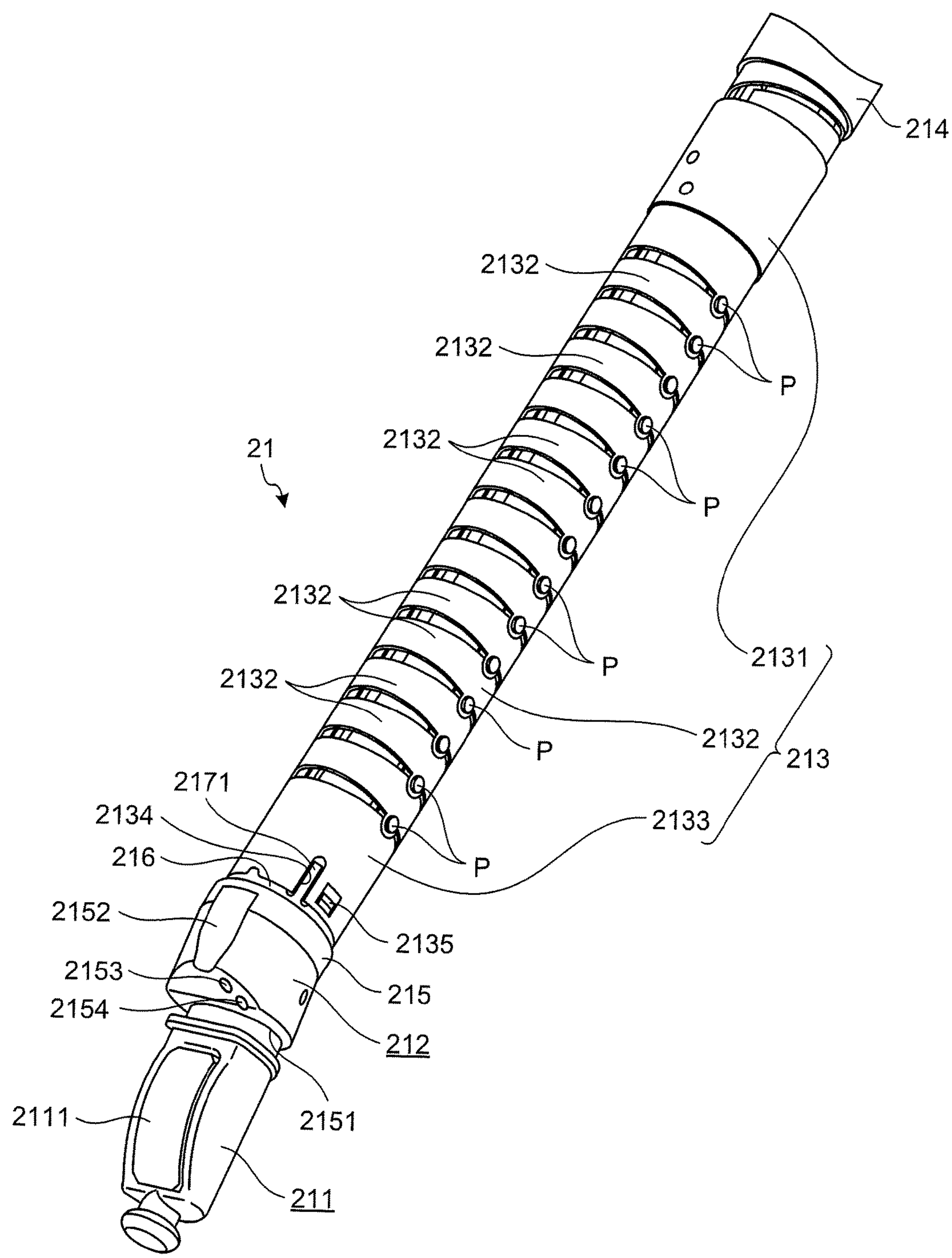
FIG. 2 is an enlarged perspective view of a distal end side of an insertion section illustrated in FIG. 1.

FIG. 2 is an enlarged perspective view of the distal end side of the insertion section 21.

Configurations of the ultrasound probe 211, the hard member 212, and the bending section 213 will be sequentially described below.

Configuration of Ultrasound Probe

As illustrated in FIG. 2, the ultrasound probe 211 is a convex ultrasound probe, and has a transducer unit 2111 in which multiple ultrasound transducers are regularly disposed to form a convex arcuate shape.

Here, an ultrasound transducer has an acoustic lens, a piezoelectric element, and a matching layer, and obtains an ultrasound echo contributing to an ultrasound tomographic image captured inside the body wall in the subject.

The transducer unit 2111 converts the pulse signal, which is input from the ultrasound observation device 3 through the signal cable provided inside the insertion section 21, into ultrasound pulses, and transmits the ultrasound pulses to the subject. Furthermore, the transducer unit 2111 converts the ultrasound echo reflected from the subject into an electrical echo signal, and outputs the echo signal to the ultrasound observation device 3 through the signal cable provided inside the insertion section 21.

Configuration of Hard Member

Figure 3:
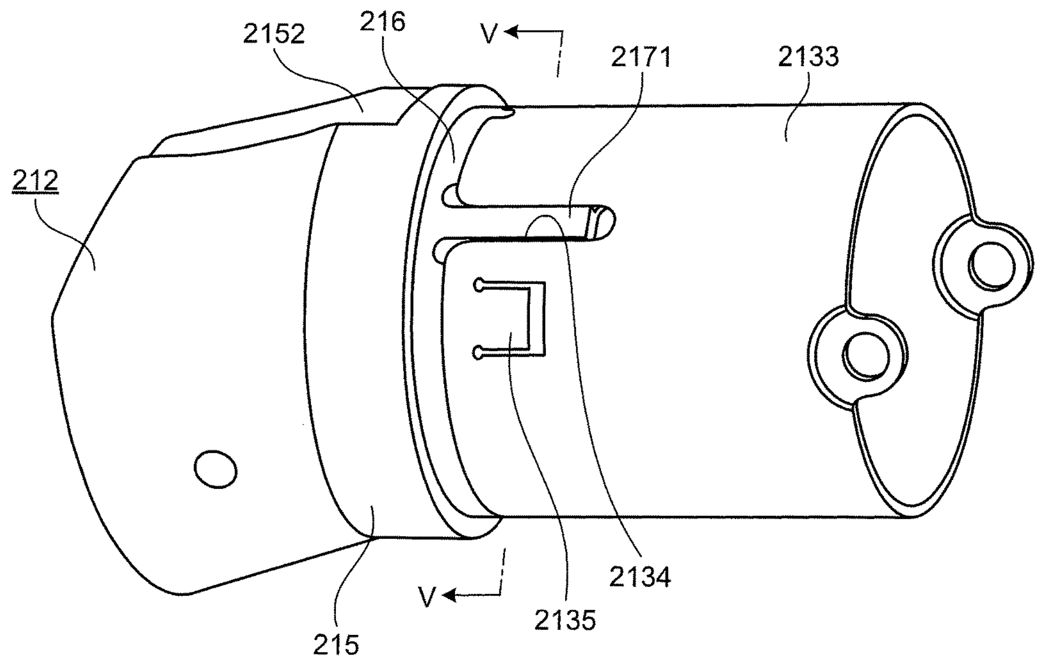
FIG. 3 is a perspective view of a state in which a distal end base of a bending section illustrated in FIGS. 1 and 2 is connected to a hard member illustrated in FIGS. 1 and 2, when viewed from a proximal end side.
Figure 4:
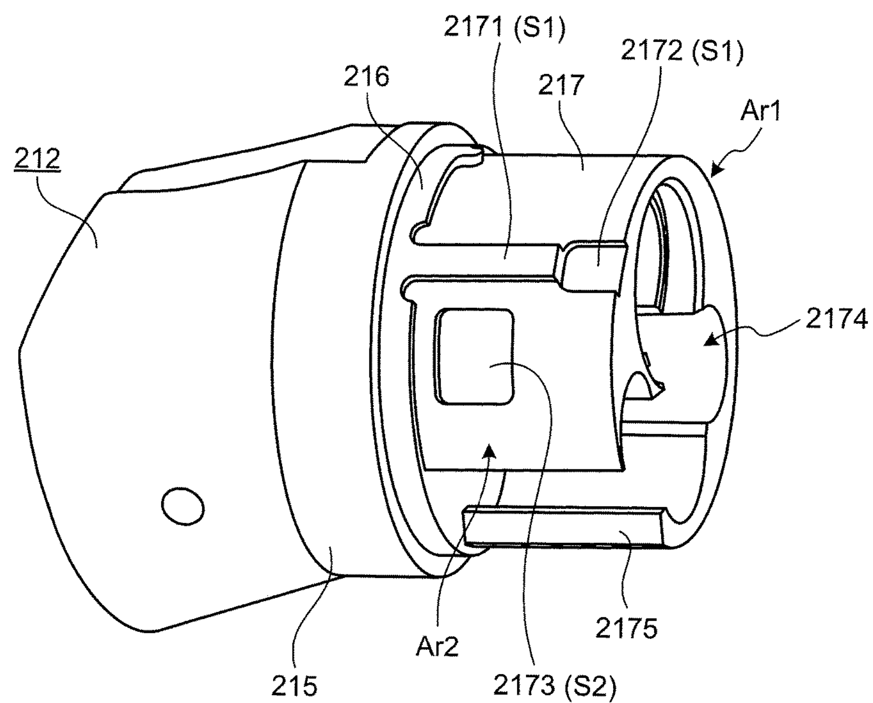
FIG. 4 is a perspective view of the hard member illustrated in FIGS. 1 to 3, when viewed from the proximal end side.
Figure 5:
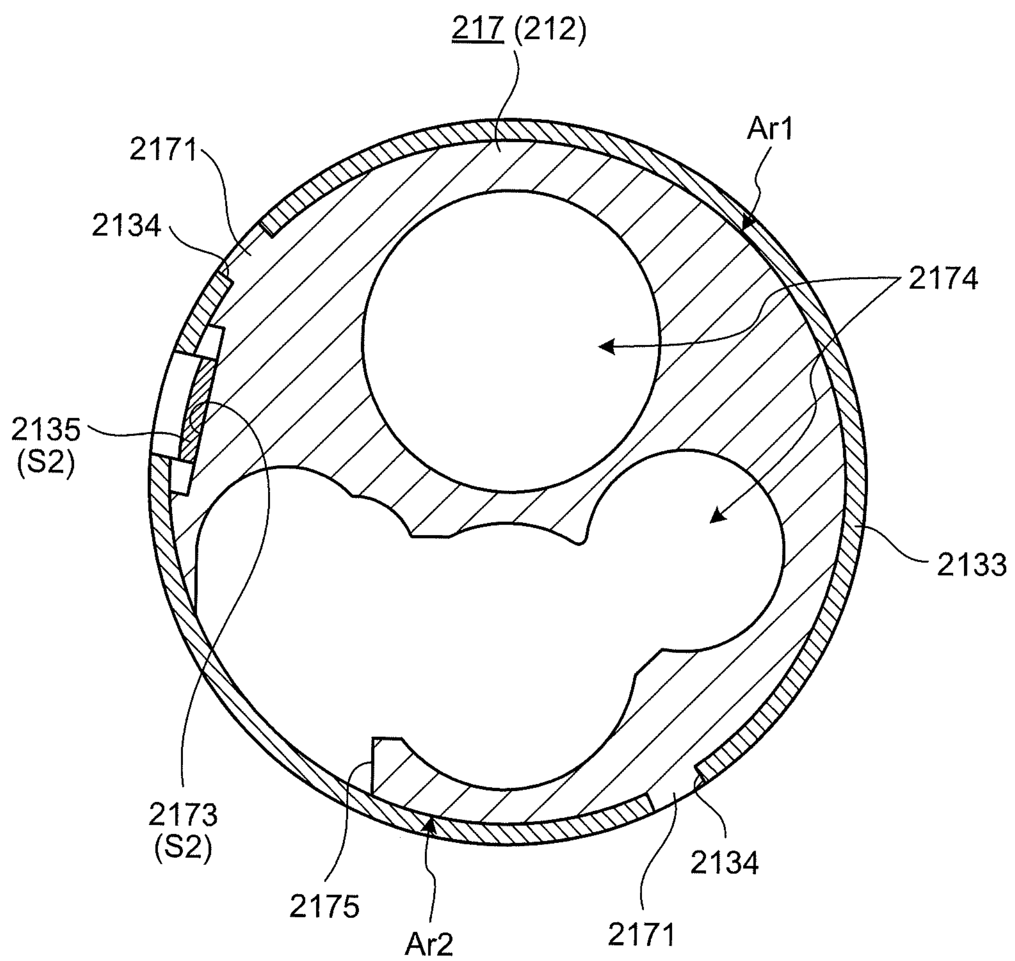
FIG. 5 is a cross-sectional view taken along a line V-V of FIG. 3.

FIG. 3 is a perspective view of a state in which a distal end base 2133 of the bending section 213 is connected to the hard member 212, when viewed from the proximal end side. FIG. 4 is a perspective view of the hard member 212 when viewed from the proximal end side. FIG. 5 is a cross-sectional view taken along a line V-V of FIG. 3.

The hard member 212 is a hard member made of a resin material. As illustrated in FIGS. 2 to 5, the hard member 212 includes a large diameter portion 215 (FIGS. 2 to 4), an intermediate diameter portion 216 (FIGS. 2 to 4), and a small diameter portion 217 (FIGS. 4 and 5).

As illustrated in FIGS. 2 to 4, the large diameter portion 215 is positioned on a distal end side of the hard member 212, and having a substantially columnar shape. Furthermore, as illustrated in FIG. 2, in the large diameter portion 215, a mounting hole 2151, a treatment tool channel 2152, an imaging hole 2153, and an illumination hole 2154 are formed. The ultrasound probe 211 is mounted into the mounting hole 2151, the treatment tool channel 2152 protrudes, to the outside, various treatment tools inserted through the treatment tool insertion passage, the imaging hole 2153 having an optical system, an imaging sensor, or the like disposed therein, and imaging inside the subject, and the illumination hole 2154 illuminates inside the subject with illumination light supplied from the light source device 6.

As illustrated in FIGS. 2 to 4, the intermediate diameter portion 216 has a substantially columnar shape having an outer diameter smaller than that of the large diameter portion 215, and is integrally formed on a proximal end side of the large diameter portion 215, coaxially with the large diameter portion 215.

As illustrated in FIG. 4 or 5, the small diameter portion 217 has a substantially columnar shape having an outer diameter smaller than that of the intermediate diameter portion 216, and is integrally formed on a proximal end side of the intermediate diameter portion 216, coaxially with the intermediate diameter portion 216. Furthermore, the small diameter portion 217 has a function as the fitting portion according to the present invention.

As illustrated in FIGS. 2 to 5, two dam portions 2171, two storage portions 2172 (FIG. 4), a swaging recess portion 2173 (FIGS. 4 and 5), a housing portion 2174 (FIGS. 4 and 5), and a cut-out portion 2175 (FIGS. 4 and 5) are formed, in the small diameter portion 217.

As illustrated in FIG. 5, the two dam portions 2171 are formed at positions on the outer surface of the small diameter portion 217, slightly displaced from positions opposite to each other about a central axis of the small diameter portion 217. That is, the outer surface of the small diameter portion 217 is divided into a first area Ar1 (FIGS. 4 and 5), and a second area Ar2 (FIGS. 4 and 5) having an area smaller than that of the first area Ar1, by the two dam portions 2171. Since the two dam portions 2171 have the same shape, hereinafter, the shape of only one of the dam portions 2171 will be described.

As illustrated in FIGS. 2 to 5, the dam portion 2171 is a projection projecting from the outer surface of the small diameter portion 217, and has a shape having one end connected to the intermediate diameter portion 216, and linearly extending toward the proximal end side from the one end, along the central axis of the small diameter portion 217 (corresponding to "axial direction of the insertion section" according to the present invention). Furthermore, the dam portion 2171 has a function of blocking the adhesive applied on the outer surface of the small diameter portion 217 and flowing to the cut-out portion 2175.

As illustrated in FIG. 4, the two storage portions 2172 are continuously provided to the two dam portions 2171, in the outer surface of the small diameter portion 217. In FIG. 4, only one storage portion 2172 of the two storage portions 2172 is illustrated for convenience of description. Furthermore, since the two storage portions 2172 have the same shape, hereinafter, the shape of only one of the storage portions 2172 will be described.

As illustrated in FIG. 4, the storage portion 2172 is a recessed portion provided in the outer surface of the small diameter portion 217, and continuously provided on the proximal end side of the dam portion 2171 (corresponding to "the leading end side of the fitting portion" according to the present invention) so that the storage portion 2172 partially opposed to the other end of the dam portion 2171. Furthermore, the storage portion 2172 has a function of partially storing the adhesive blocked by the dam portion 2171.

The dam portion 2171 and the storage portion 2172 described above constitute an unnecessary-adhesion preventing structure S1 according to the present invention (FIG. 4).

As illustrated in FIG. 4 or 5, the swaging recess portion 2173 is a recessed portion provided in the second area Ar2 of the first and second areas Ar1 and Ar2, on the outer surface of the small diameter portion 217. Furthermore, the swaging recess portion 2173 partially constitutes a connection structure S2 according to the present invention (FIGS. 4 and 5).

As illustrated in FIG. 4 or 5, the housing portion 2174 extends inward from an end surface of the small diameter portion 217 (corresponding to "the leading end of the fitting portion" according to the present invention). Furthermore, the housing portion 2174 communicates with the mounting hole 2151, the treatment tool channel 2152, the imaging hole 2153, and the illumination hole 2154 disposed in the large diameter portion 215. That is, the housing portion 2174 is a portion through which the light guide and the plurality of signal cables provided inside the insertion section 21, and the treatment tool are inserted.

As illustrated in FIG. 4 or 5, the cut-out portion 2175 is formed by cutting out a portion of the small diameter portion 217 from the end surface to the intermediate diameter portion 216, to communicate inside and outside of the housing portion 2174 with each other. Furthermore, the cut-out portion 2175 is provided in the second area Ar2 of the first and second areas Ar1 and Ar2, on the outer surface of the small diameter portion 217.

Configuration of Bending Section

As illustrated in FIGS. 2 and 3 or 5, the bending section 213 includes a proximal end base 2131 (FIG. 2), a plurality of ring-shaped members 2132 (FIG. 2), and the distal end base 2133.

The proximal end base 2131 has a cylindrical shape, and is connected to the flexible tube portion 214, on the proximal end side.

In the plurality of ring-shaped members 2132, adjacent ring-shaped members 2132 are partially connected by pins P turnably (vertically turnably in FIG. 2) to have a substantially cylindrical shape as a whole, and the plurality of ring-shaped members 2132 is connected to the proximal end base 2131 on the proximal end side.

The distal end base 2133 is made of a metal material such as stainless steel. Furthermore, the distal end base 2133 is formed into a cylindrical shape having an inner diameter slightly larger than the outer diameter of the small diameter portion 217, and an outer diameter substantially the same as the outer diameter of the intermediate diameter portion 216, and the proximal end side of the distal end base 2133 is connected by pins P turnably (vertically turnably in FIG. 2), on the distal end side of the plurality of ring-shaped members 2132. The distal end base 2133 has a function as the connection member according to the present invention.

Furthermore, in the above-mentioned proximal end base 2131, plurality of ring-shaped members 2132, and distal end base 2133, two angle wires (not illustrated) are inserted, in addition to the light guide, the plurality of signal cables, and the treatment tool. The two angle wires each have one end connected to the bending knob 221, and the other end connected to the distal end base 2133. That is, when the physician or the like operates the bending knob 221, the two angle wires are appropriately pulled and released, and the bending section 213 is bent in an upward direction or a downward direction, in FIG. 2.

Furthermore, as illustrated in FIGS. 2 and 3 or 5, two opening portions 2134 and a swaging tab portion 2135 are formed, in the distal end base 2133.

The two opening portions 2134 are portions formed by cutting out the distal end base 2133 from the distal end side, to receive insertion of the two dam portions 2171, and the two opening portions 2134 are provided at positions corresponding to the two dam portions 2171 in the small diameter portion 217.

The swaging tab portion 2135 is a portion having a base end portion connected to the distal end base 2133, and a leading end portion separated from the distal end base 2133 and swaged onto the swaging recess portion 2173, and the swaging tab portion 2135 is provided at a position corresponding to the swaging recess portion 2173 in the small diameter portion 217. The swaging tab portion 2135 is formed by cutting the distal end base 2133 into U-shape so that the leading end portion is directed toward the proximal end side.

The above-mentioned swaging tab portion 2135 and swaging recess portion 2173 constitute the connection structure S2 of the present invention (FIG. 5).

Method for Connecting Hard Member and Distal End Base

Next, a connection method for the above-mentioned hard member 212 and distal end base 2133 will be described.

First, the worker applies the adhesive to the first area Ar1 on the outer surface of the small diameter portion 217. The adhesive is not applied to the second area Ar2. That is, the first area Ar1 corresponds to an application area according to the present invention. Furthermore, the second area Ar2 corresponds to a non-application area according to the present invention.

Next, the worker positions the two opening portions 2134 to the two dam portions 2171 to fit the small diameter portion 217 into the distal end base 2133.

Next, the worker presses the swaging tab portion 2135 to fit the swaging tab portion 2135 into the swaging recess portion 2173.

Through the above-mentioned process, the hard member 212 and the distal end base 2133 are connected to each other.

Configurations of First and Second Connector Portions

Structures of the first and second connector portions 241 and 242 will be described below.

Figure 6:
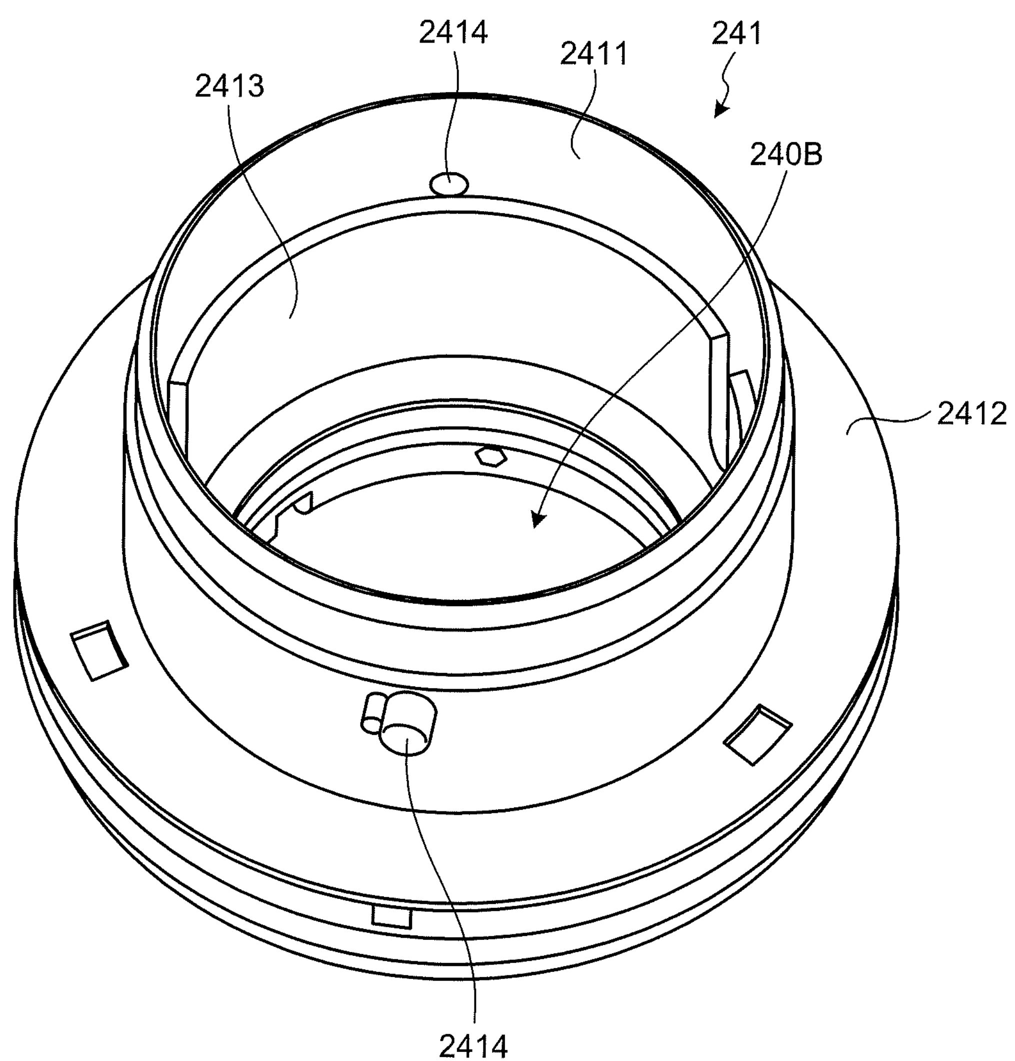
FIG. 6 is a perspective view illustrating an internal structure of a first connector portion illustrated in FIG. 1.

FIG. 6 is a perspective view illustrating an internal structure of the first connector portion 241.

The first and second connector portions 241 and 242 have a substantially similar shape. Therefore, only a structure of the first connector portion 241 will be described below.

The first connector portion 241 is an electrical connector for electrically connecting a signal cable inserted into the universal cable 23, and the ultrasound cable 31. As illustrated in FIG. 6, the first connector portion 241 has a cylindrical shape covering a terminal Te (see FIG. 8) electrically connected to the ultrasound cable 31.

Although not specifically illustrated, the terminal Te is disposed to liquid-tightly seal the inside of the first connector portion 241 with an O-ring or the like.

The first connector portion 241 includes a connection portion 2411 connected to a connector portion (not illustrated) of the ultrasound cable 31, and a protruding portion 2412 protruding outward from a proximal end (lower end portion in FIG. 6) of the connection portion 2411. Furthermore, in the first connector portion 241, an aperture 240B (see FIG. 6) is formed in a connector case 240A (see FIG. 8) constituting the connector 24, and the protruding portion 2412 is fitted into the aperture 240B to liquid-tightly seal the aperture 240B with an O-ring or the like.

As illustrated in FIG. 6, the connection portion 2411 has an inner surface, and a cylindrical sleeve 2413 is liquid-tightly mounted on the inner surface with an O-ring or the like.

Furthermore, as illustrated in FIG. 6, in the connection portion 2411, two locking pins 2414 for locking a connector cap 244 (see FIG. 7) to the first connector portion 241 are mounted so that the locking pins 2414 project from an outer surface of the connection portion 2411.

In the endoscope 2, the ultrasound cable 31, the video cable 41, and the optical fiber cable 61 are removed from the first to third connector portions 241 to 243, and so-called autoclave sterilization or sterilization by antiseptic solution is performed thereon, before ultrasonic diagnosis in the subject, Upon sterilization, water or liquid such as the antiseptic solution tends to enter the first and second connector portions 241 and 242. Although not specifically illustrated, unlike the first and second connector portions 241 and 242, the third connector portion 243 does not have an opened connector structure (structure in which water or liquid such as the antiseptic solution easily enter).

Therefore, for disinfection or sterilization, in order to prevent entrance of a liquid into the first and second connector portions 241 and 242, the connector caps 244 (see FIG. 7) are mounted to the first and second connector portions 241 and 242.

Configuration of Connector Cap

The connector caps 244 mounted to the first and second connector portions 241 and 242 have a substantially similar structure. Therefore, only a structure of the connector cap 244 mounted to the first connector portion 241 will be described below.

Figure 7:
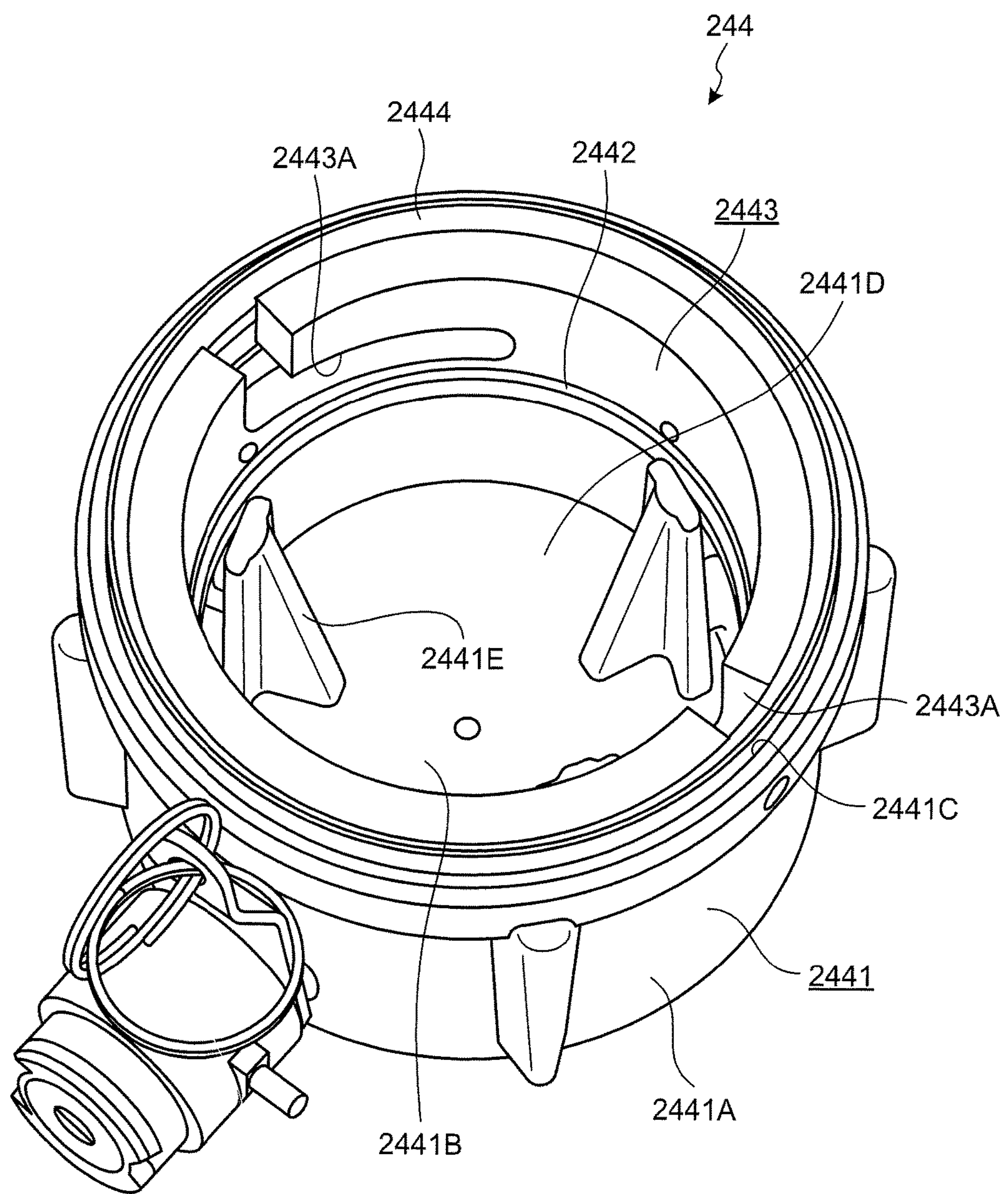
FIG. 7 is a perspective view illustrating an internal structure of a connector cap mounted to the first connector portion illustrated in FIG. 6.
Figure 8:
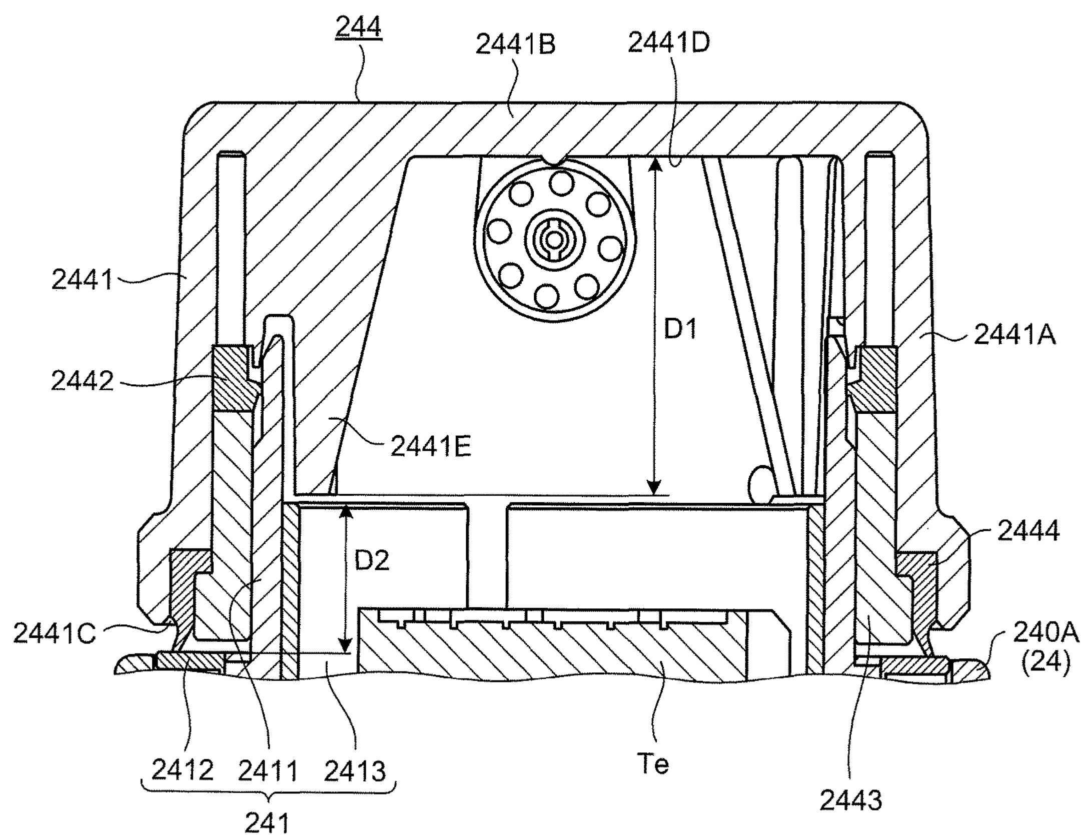
FIG. 8 is a cross-sectional view of a state in which the connector cap illustrated in FIG. 7 is mounted to the first connector portion illustrated in FIG. 6.

FIG. 7 is a perspective view illustrating an internal structure of the connector cap 244 mounted to the first connector portion 241. FIG. 8 is a cross-sectional view of a state in which the connector cap 244 is mounted to the first connector portion 241.

As illustrated in FIG. 7 or 8, the connector cap 244 includes a cap body 2441, a first packing 2442, a cam body 2443, and a second packing 2444.

As illustrated in FIG. 7 or 8, the cap body 2441 is formed into a container shape including a cylindrical side wall portion 2441A for inserting the connection portion 2411 therein, and a bottom portion 2441B closing one end of the side wall portion 2441A, and having an opening portion 2441C in the other end of the side wall portion 2441A.

The bottom portion 2441B has an inner surface 2441D (bottom surface of the cap body 2441) on which standing ribs 2441E are provided. Furthermore, as illustrated in FIG. 8, each of the ribs 2441E is positioned to have a predetermined gap between a leading end of the rib 2441E and a leading end of the sleeve 2413 (upper end portion in FIGS. 6 and 8), upon mounting the connector cap 244 to the first connector portion 241.

The first packing 2442 has a ring shape, and mounted on an inner surface of the side wall portion 2441A. Furthermore, as illustrated in FIG. 8, when the connector cap 244 is mounted to the first connector portion 241, the first packing 2442 makes contact with the outer surface of the connection portion 2411 to maintain liquid tightness in the first connector portion 241.

The cam body 2443 has a cylindrical shape for inserting the connection portion 2411 therein, and is mounted on the inner surface of the side wall portion 2441A, on the side of the opening portion 2441C. As illustrated in FIG. 7, in the cam body 2443, two locking grooves 2443A are formed, and two locking pins 2414 are respectively inserted into the two locking grooves 2443A.

As illustrated in FIG. 7, each of the two locking grooves 2443A has a substantially L-shape extending from one end (end portion on the side of the opening portion 2441C) to the other end (end portion on the side of the bottom portion 2441B), and extending in a rotation direction about a central axis of the cam body 2443 (not illustrated). That is, in the first embodiment, as a locking structure between the first connector portion 241 and the connector cap 244, a bayonet locking structure is employed.

The second packing 2444 has a ring shape, and is mounted in the opening portion 2441C to be partially inserted into a gap between the cam body 2443 and the inner surface of the side wall portion 2441A. Furthermore, as illustrated in FIG. 8, when the connector cap 244 is mounted to the first connector portion 241, the second packing 2444 makes contact with the protruding portion 2412 to maintain liquid tightness in the first connector portion 241.

The first connector portion 241 and connector cap 244 described above is designed to have the following dimensional relationship for each product type of the endoscope 2.

When a height between the inner surface 2441D of the bottom portion 2441B and the leading end of the rib 2441E is denoted by D1 (FIG. 8), and a height between the protruding portion 2412 and the leading end of the sleeve 2413 is denoted by D2 (FIG. 8), the first connector portion 241 and connector cap 244 are designed to have a dimensional relationship satisfying the following formula (1).

$$\text{Specified value } Va = D1 + D2 \qquad (1)$$

The specified value Va varies depending on product types of the endoscope 2.

Owing to such a dimensional relationship, when the first connector portion 241 and the connector cap 244 of the same product type are connected to each other, a slight gap is generated between the protruding portion 2412 and the other end of the side wall portion 2441A (end portion on the side of the opening portion 2441C), as illustrated in FIG. 8.

Figure 9:
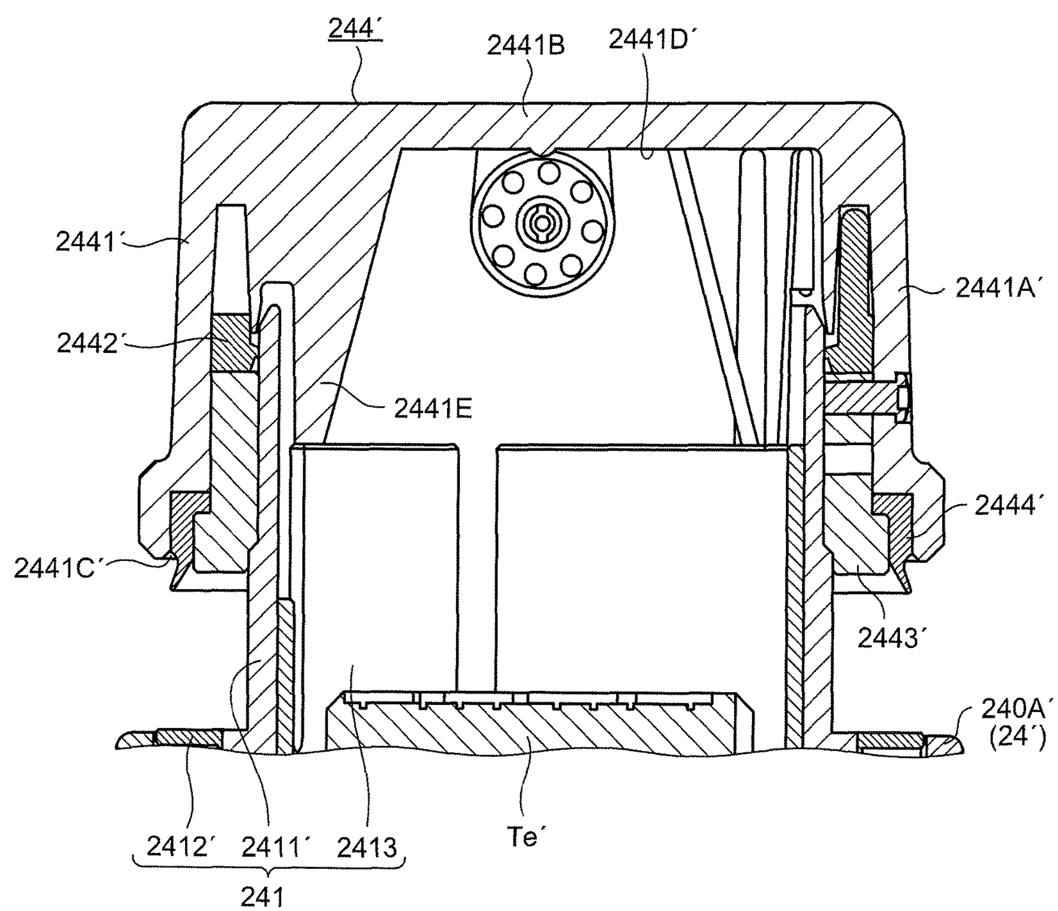
FIG. 9 is a cross-sectional view of a state in which a first connector portion and a connector cap of different product types are connected to each other.

FIG. 9 is a cross-sectional view of a state in which a first connector portion 241' and a connector cap 244' of different product types are connected to each other.

In order to distinguish from the first connector portion 241 and the connector cap 244 described in FIGS. 6 to 8, corresponding members are denoted by reference signs with "'" in FIG. 9.

In contrast, when the first connector portion 241' and the connector cap 244' of different product types are connected to each other, since the first connector portion 241' and the connector cap 244' have different product types, the dimensional relationship of formula (1) is not satisfied, and a larger gap is generated between the protruding portion 2412' and the other end of the side wall portion 2441A', as illustrated in FIG. 9.

That is, the worker who mounts the connector cap 244 or 244' to the first connector portion 241 or 241' can determine that the connector cap 244 of the same product type is mounted, when the slight gap is generated, and that the connector cap 244' of different product type is mounted, when the larger gap is generated.

Even if the first connector portion 241' and the connector cap 244' of different product types are connected, a dimension of each portion is designed to be appropriately set so that a rib 2441E' makes contact with a leading end of a sleeve 2413' to maintain liquid tightness in the first connector portion 241', as illustrated in FIG. 9.

In the endoscope 2 according to the first embodiment described above, in the small diameter portion 217, the cut-out portion 2175 is formed by cutting out the portion of the small diameter portion 217 from the end surface to communicate inside and outside of the housing portion 2174 with each other. Therefore, the wall thickness of part of the small diameter portion 217 (part of a portion surrounding the housing portion 2174) can be removed, and reduction in diameter (reduction in size) of the small diameter portion 217 can be achieved due to the removed wall thickness.

Furthermore, in the endoscope 2, the small diameter portion 217 is provided with the unnecessary-adhesion preventing structure S1 having the dam portion 2171 and the storage portion 2172. Therefore, even if the adhesive flows out along the outer surface of the small diameter portion 217, the dam portion 2171 can prevent the adhesive from flowing toward the cut-out portion 2175. That is, the adhesive is prevented from adhering to the light guide, the plurality of signal cables, or the treatment tool disposed in the housing portion 2174, through the cut-out portion 2175. Furthermore, the storage portion 2172 is continuously provided on the proximal end side relative to the dam portion 2171, and since the storage portion 2172 partially stores the adhesive blocked by the dam portion 2171, the adhesive can be also prevented from flowing to the end surface of the small diameter portion 217, and adhering to the light guide, the plurality of signal cables, or the treatment tool disposed in the housing portion 2174.

Thus, according to the endoscope 2 of the first embodiment, the size of the hard member 212 can be reduced, and the adhesive can be prevented from adhering to the light guide, the plurality of signal cables, or the treatment tool disposed in the hard member 212, in an effective manner.

Furthermore, in the endoscope 2 according to the first embodiment, the small diameter portion 217 and the distal end base 2133 are provided with the connection structure S2. Therefore, the hard member 212 and the distal end base 2133 can be secured to each other with the connection structure S2, in addition to the adhesive, and the hard member 212 and the distal end base 2133 can be firmly secured to each other.

In particular, the connection structure S2 is provided in the second area Ar2 as the non-application area to which no adhesive is applied. Therefore, in comparison with a configuration having the connection structure S2 provided in the first area Ar1 as the application area to which the adhesive is applied, when a component of the hard member 212 or the distal end base 2133 is changed, the hard member 212 and the distal end base 2133 can be readily removed.

Second Embodiment

Next, a second embodiment of the present invention will be described.

In the following description, elements similar to those of the first embodiment described above are denoted by the same reference signs, and detailed description thereof will be omitted or simplified.

In the endoscope 2 according to the first embodiment described above, as the storage portion according to the present invention, the recessed portion (storage portion 2172) formed in the outer surface of the small diameter portion 217 is employed.

In contrast, in an endoscope according to the second embodiment, a porous member provided independently of a hard member and a distal end base is employed as the storage portion according to the present invention.

A distal end base according to the second embodiment has a configuration similar to that of the distal end base 2133 described in the first embodiment.

A configuration of the hard member according to the second embodiment will be described below.

Configuration of Hard Member

Figure 10:
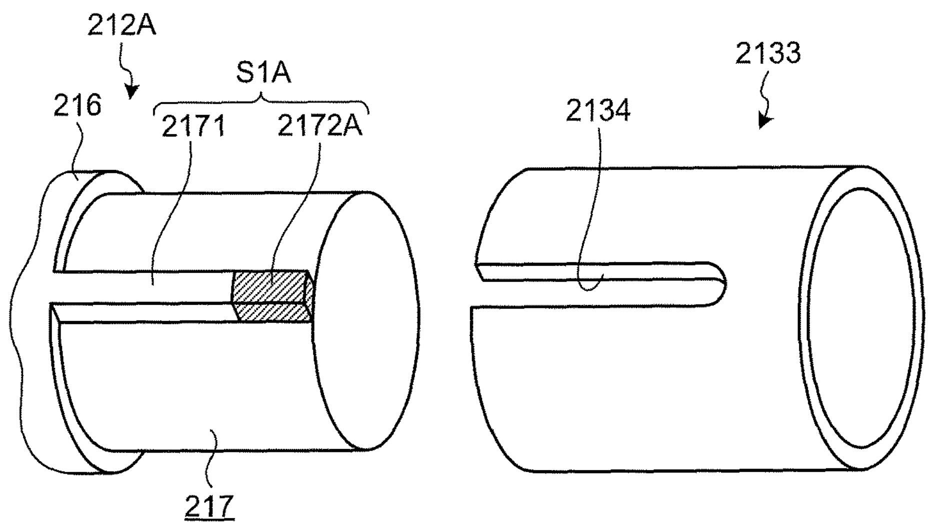
FIG. 10 is an exploded perspective view schematically illustrating a hard member and a distal end base according to a second embodiment of the present invention.

FIG. 10 is an exploded perspective view schematically illustrating a hard member 212A and the distal end base 2133 according to the second embodiment of the present invention.

The hard member 212A has a configuration similar to that of the hard member 212 described in the above first embodiment, except for the storage portion 2172.

In FIG. 10, as the configuration of the hard member 212A, only one dam portion 2171 is illustrated while the swaging recess portion 2173, the housing portion 2174, and the cut-out portion 2175 is not illustrated for convenience of explanation. As a configuration of the distal end base 2133, only one opening portion 2134 is illustrated while the swaging tab portion 2135 is not illustrated.

In the hard member 212A, on the outer surface of the small diameter portion 217, a storage portion 2172A is mounted to be continuously provided on the proximal end side of the dam portion 2171, as illustrated in FIG. 10.

The storage portion 2172A is made of sponge or the like having a width substantially the same as that of the dam portion 2171 to be inserted into the opening portion 2134. The storage portion 2172A has a function similar to the function of the storage portion 2172 described in the first embodiment.

Furthermore, the dam portion 2171 and the storage portion 2172 A constitute an unnecessary-adhesion preventing structure S1A according to the present invention (FIG. 10).

Even if the unnecessary-adhesion preventing structure S1A as described in the second embodiment is employed, effects similar to those of the above first embodiment can be obtained.

Modification 2-1 of Second Embodiment

Figure 11:
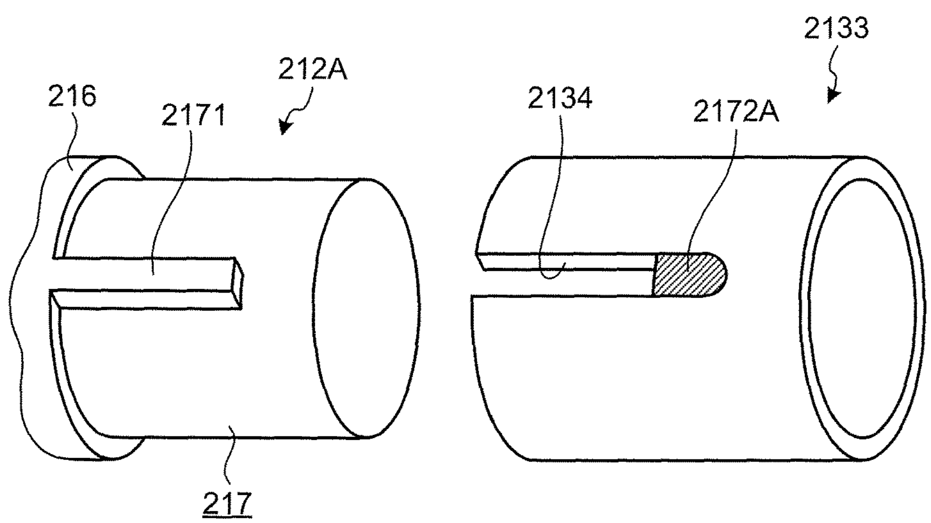
FIG. 11 is a diagram illustrating modification 2-1 of the second embodiment of the present invention.

FIG. 11 is a diagram illustrating modification 2-1 of the second embodiment of the present invention. In particular, FIG. 11 is a figure corresponds to FIG. 10.

In the above second embodiment, the storage portion 2172A is mounted to the hard member 212A, but is not limited to this configuration, and may be mounted to the proximal end side of the opening portion 2134, that is, to the distal end base 2133, as illustrated in FIG. 11.

Modification 2-2 of Second Embodiment

In the above second embodiment, the dam portion 2171 is integrally formed on the hard member 212A, but is not limited to this configuration, and may be provided independently of the hard member 212A to be mounted to the hard member 212A, similarly to the storage portion 2172A.

Here, a material of the dam portion 2171 provided independently of the hard member 212A may be the same as that of the hard member 212A, or may be different from that of the hard member 212A.

The dam portion 2171 in the above first embodiment may also be provided independently of the hard member 212.

Third Embodiment

Next, a third embodiment of the present invention will be described.

In the following description, elements similar to those of the first embodiment described above are denoted by the same reference signs, and detailed description thereof will be omitted or simplified.

In the endoscope 2 according to the first embodiment described above, the projection (dam portion 2171) projecting from the outer surface of the small diameter portion 217 is employed, as the dam portion according to the present invention.

In contrast, in an endoscope according to the third embodiment, the dam portion according to the present invention is integrally formed with the distal end base.

Configurations of the hard member and the distal end base according to the third embodiment will be described below.

Configuration of Hard Member

Figure 12:
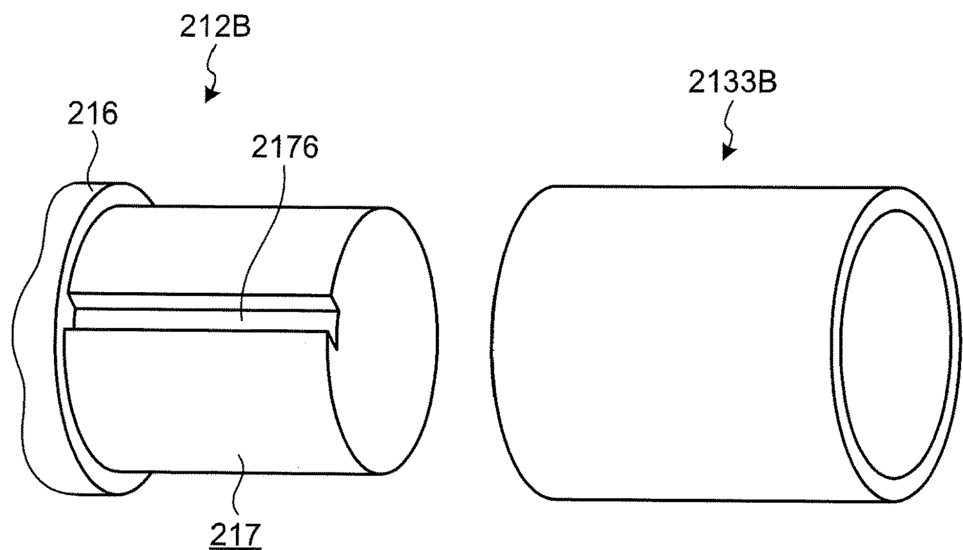
FIG. 12 is an exploded perspective view schematically illustrating a hard member and a distal end base according to a third embodiment of the present invention.

FIG. 12 is an exploded perspective view schematically illustrating a hard member 212B and a distal end base 2133B according to the third embodiment of the present invention.

The hard member 212B has a configuration similar to that of the hard member 212 described in the first embodiment, except that the two dam portions 2171 and the two storage portions 2172 are not provided, and instead, groove portions 2176 (FIG. 12) are formed at positions where the dam portions 2171 and storage portions 2172 are provided.

In FIG. 12, as a configuration of the hard member 212B, only one of the two groove portions 2176 is illustrated while the swaging recess portion 2173, the housing portion 2174, and the cut-out portion 2175 are not illustrated for convenience of description.

As illustrated in FIG. 12, the groove portion 2176 is formed to linearly extend from the end surface of the small diameter portion 217 to the intermediate diameter portion 216, along the central axis of the small diameter portion 217.

Configuration of Distal End Base

Figure 13:
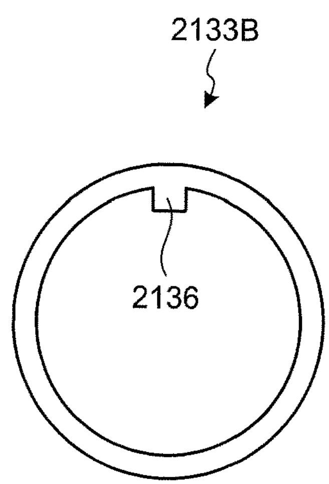
FIG. 13 is a diagram of the distal end base illustrated in FIG. 12, viewed from a direction along a central axis.

FIG. 13 is a diagram of the distal end base 2133B viewed from a direction along the central axis.

The distal end base 2133B has a configuration similar to that of the distal end base 2133 described in the first embodiment, except that the two opening portions 2134 are not provided, and instead, dam portions 2136 (FIG. 13) are formed at positions where the opening portions 2134 are provided.

In FIGS. 12 and 13, as a configuration of the distal end base 2133B, only one of the two dam portions 2136 is illustrated while the swaging tab portion 2135 is not illustrated for convenience of description.

As illustrated in FIG. 13, the dam portion 2136 is a projection projecting from an inner surface of the distal end base 2133B, and inserted into the groove portion 2176, and has a shape linearly extending from one end of the distal end base 2133B (end portion on the distal end side) to the other end of the distal end base 2133B (end portion on the proximal end side), along the central axis of the distal end base 2133B. The dam portion 2136 has a function similar to that of the dam portion 2171 described in the first embodiment.

A connection method for the hard member 212B and the distal end base 2133B is similar to the connection method for the hard member 212 and the distal end base 2133 described in the first embodiment, except that the two dam portions 2136 are positioned to the two groove portions 2176.

Figure 14:
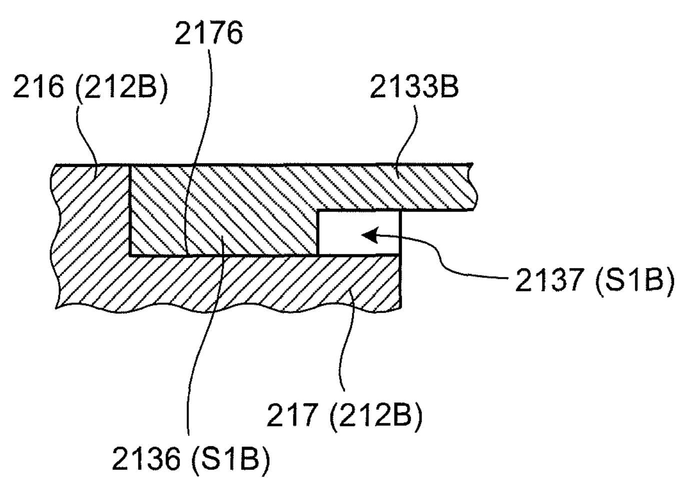
FIG. 14 is a cross-sectional view of a state in which the distal end base illustrated in FIG. 12 or 13 is connected to a hard member illustrated in FIG. 12.

FIG. 14 is a cross-sectional view of a state in which the distal end base 2133B is connected to the hard member 212B. In particular, FIG. 14 illustrates a state in which the dam portion 2136 is inserted into the groove portion 2176.

As illustrated in FIG. 14, the dam portion 2136 is formed to have a length smaller than a length of the groove portion 2176. Therefore, while the distal end base 2133B is connected to the hard member 212B, a distal end side of the dam portion 2136 makes contact with the intermediate diameter portion 216, and a space 2137 in which the dam portion 2136 is not disposed is formed on a proximal end side of the groove portion 2176. This space 2137 has a function similar to that of the storage portion 2172 described in the first embodiment.

Furthermore, the dam portion 2136 and the space 2137 constitute an unnecessary-adhesion preventing structure S1B (FIG. 14) according to the present invention.

Even if the unnecessary-adhesion preventing structure S1B as described in the third embodiment is employed, effects similar to those of the above first embodiment can be obtained.

Modification 3-1 of Third Embodiment

In the above third embodiment, the storage portion 2172A described in the above second embodiment may be mounted on the inner surface of the distal end base 2133B to be continuously provided on a proximal end side of the dam portion 2136.

Furthermore, in the above third embodiment, the dam portion 2136 may be provided independently of the distal end base 2133B to be mounted on the inner surface of the distal end base 2133B, similarly to modification 2-2 of the above second embodiment.

Other Embodiments

The embodiments for carrying out the present invention have been described above, but it should be understood that the present invention is not limited only to the above-mentioned first to third embodiments and the modifications 2-1, 2-2, and 3-1.

In the first to third embodiments and modifications 2-1, 2-2, and 3-1 described above, the endoscope system 1 has both of the function of generating the ultrasound image, and the function of generating the endoscopic image, but the endoscope system 1 is not limited to this configuration, and may be configured to have only one of the functions.

In the above first to third embodiments or modifications 2-1, 2-2, and 3-1, two of each of the dam portion 2171 or 2136, the storage portion 2172 or 2172A, the opening portion 2134, and the groove portion 2176 are provided, but a configuration is not limited to this, and only one of each of them may be provided.

An endoscope according to some embodiments includes a fitting portion (hard member) having a cut-out portion. The cut-out portion is formed by cutting out part of the fitting portion from the leading end to communicate inside and outside of the housing portion with each other. It is therefore possible to reduce a wall thickness of part of the fitting portion (part of a portion surrounding the housing portion) can be removed, thereby to achieve a small-sized fitting portion (hard member).

Furthermore, according to the endoscope of some embodiments, at least one of the fitting portion and a connection member includes an unnecessary-adhesion preventing structure having a dam portion and a storage portion. With this structure, even if the adhesive flows out along an outer surface of the fitting portion, the dam portion can prevent the adhesive from flowing toward the cut-out portion. That is, the adhesive is prevented from adhering to the internal components disposed in the housing portion through the cut-out portion. Furthermore, since the storage portion partially stores the adhesive blocked by the dam portion, the adhesive can be also prevented from flowing to the leading end of the fitting portion and adhering to the internal components disposed in the housing portion.

Thus, according to the endoscope of some embodiments, it is possible to achieve a small-sized hard member, and to prevent the adhesive from adhering to the internal components disposed in the hard member, in an effective manner.

Because the hard member according to some embodiments is used for the endoscope described above, similar effects to those of the endoscope described above can be obtained.

In the first to third embodiments and modifications 2-1, 2-2, and 3-1 described above, the endoscope system 1 is not limited to medical field use, and the endoscope system 1 may be used in an industrial field, to be used as an endoscope system for observing inside a subject such as a machine structure.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

Reference Signs List

1 ENDOSCOPE SYSTEM
2 ENDOSCOPE
3 ULTRASOUND OBSERVATION DEVICE
4 ENDOSCOPE OBSERVATION DEVICE
5 DISPLAY DEVICE
6 LIGHT SOURCE DEVICE
21 INSERTION SECTION
22 OPERATING UNIT
23 UNIVERSAL CABLE
24, 24' CONNECTOR
31 ULTRASOUND CABLE
41 VIDEO CABLE
61 OPTICAL FIBER CABLE
211 ULTRASOUND PROBE
212, 212A, 212B HARD MEMBER
213 BENDING SECTION
214 FLEXIBLE TUBE PORTION
215 LARGE DIAMETER PORTION
216 INTERMEDIATE DIAMETER PORTION
217 SMALL DIAMETER PORTION
221 BENDING KNOB
222 OPERATION MEMBER
223 TREATMENT TOOL INSERTION OPENING
240A, 240A' CONNECTOR CASE
240B APERTURE
241, 241' FIRST CONNECTOR PORTION
242 SECOND CONNECTOR PORTION
243 THIRD CONNECTOR PORTION
244, 244' CONNECTOR CAP
2111 SOUND WAVE GENERATOR
2131 PROXIMAL END BASE
2132 RING-SHAPED MEMBER
2133, 2133B DISTAL END BASE
2134 OPENING PORTION
2135 SWAGING TAB PORTION
2136 DAM PORTION
2137 SPACE
2151 MOUNTING HOLE
2152 TREATMENT TOOL CHANNEL
2153 IMAGING HOLE
2154 ILLUMINATION HOLE
2171 DAM PORTION
2172, 2172A STORAGE PORTION
2173 SWAGING RECESS PORTION
2174 HOUSING PORTION
2175 CUT-OUT PORTION
2176 GROOVE PORTION
2411, 2411' CONNECTION PORTION
2412, 2412' PROTRUDING PORTION
2413, 2413' SLEEVE
2414 LOCKING PIN
2441, 2441' CAP BODY
2441A, 2441A' SIDE WALL PORTION
2441B, 2441B' BOTTOM PORTION
2441C, 2441C' OPENING PORTION
2441D, 2441D' INNER SURFACE
2441E, 2441E' RIB
2442, 2442' FIRST PACKING
2443, 2443' CAM BODY
2443A LOCKING GROOVE

2444, 2444' SECOND PACKING
Ar1 FIRST AREA
Ar2 SECOND AREA
D1, D2 HEIGHT
P PIN
S1, S1A, S1B UNNECESSARY-ADHESION PREVENTING STRUCTURE
S2 CONNECTION STRUCTURE
Te, Te' TERMINAL

What is claimed is:

1. An endoscope comprising: an insertion section configured to be inserted into a subject to observe an inside of the subject, the insertion section comprising: a bending piece comprising a cylindrical connection member; and a hard member having a fitting portion fitted into the connection member and secured to the connection member with an adhesive applied on an outer surface of the fitting portion: a dam portion extending in an axial direction of the insertion section along the outer surface of the fitting portion to block the adhesive flowing along the outer surface of the fitting portion, the dam portion being longer in the axial direction of the fitting portion than in a circumferential direction of the fitting portion; and a storage portion continuously provided to the dam portion to partially store the adhesive blocked by the dam portion, the dam portion being a projection from the outer surface of the fitting portion and extending in the axial direction of the insertion section along the outer surface of the fitting portion to block the adhesive flowing along the outer surface of the fitting portion; and the storage portion being a recessed portion recessed from the outer surface of the fitting portion and continuously provided to the dam portion to partially store the adhesive blocked by the dam portion.

2. The endoscope according to claim 1, wherein the dam portion is provided on the outer surface of the fitting portion, and the connection member comprises an opening portion into which the dam portion is inserted when the fitting portion is fitted into the connection member.

3. The endoscope according to claim 1, wherein the storage portion is continuously provided on a leading end side of the fitting portion relative to the dam portion.

4. The endoscope according to claim 1, wherein the at least one of the fitting portion and the connection member further comprises one additional dam portion to define two dam portions, wherein the two dam portions separate the outer surface of the fitting portion into an application area to which the adhesive is applied and a non-application area to which no adhesive is applied.

5. The endoscope according to claim 4, wherein the fitting portion and the connection member comprise a connection structure for swaging to connect part of the connection member to the outer surface of the fitting portion, and the connection structure is disposed on the non-application area.

6. The endoscope according to claim 4, wherein the hard member comprises: a housing portion disposed inside the hard member; and a cut-out portion disposed such that the housing portion communicates with an outside of the housing portion, wherein the cut-out portion is disposed on the non-application area.

7. An insertion section for use with an endoscope, the insertion section being configured to be inserted into a subject to observe an inside of the subject, the insertion section comprising: a bending piece comprising a cylindrical connection member; a hard member having a fitting portion fitted into the connection member and secured to the connection member with an adhesive applied on an outer surface of the fitting portion: a dam portion extending in an axial direction of the insertion section along the outer surface of the fitting portion to block the adhesive flowing along the outer surface of the fitting portion, the dam portion being longer in the axial direction of the fitting portion than in a circumferential direction of the fitting portion; and a storage portion continuously provided to the dam portion to partially store the adhesive blocked by the dam portion, the dam portion being a projection projecting from the outer surface of the fitting portion and extending in the axial direction of the insertion section along the outer surface of the fitting portion to block the adhesive flowing along the outer surface of the fitting portion; and the storage portion being a recessed portion recessed from the outer surface of the fitting portion and continuously provided to the dam portion to partially store the adhesive blocked by the dam portion.

8. The endoscope according to claim 1, further comprising a plurality of additional bending pieces pivotably connected to each other; wherein a distal-most bending piece of the plurality of additional bending pieces being pivotably connected to the connection member.

9. The insertion section according to claim 7, further comprising a plurality of additional bending pieces pivotably connected to each other; wherein a distal-most bending piece of the plurality of additional bending pieces being pivotably connected to the connection member.

10. The endoscope according to claim 1, wherein the storage portion is provided in a vicinity of the dam portion.

11. The endoscope according to claim 1, wherein the storage portion is provided on an extension line in a longitudinal direction of the dam portion that extends the axial direction of the insertion section along the outer surface of the fitting portion.

12. The endoscope according to claim 1, wherein the storage portion is provided in a position closer to a distal end than to a proximal end of the fitting portion.

13. The endoscope according to claim 1, wherein the insertion section further comprises a groove portion in the connection member, wherein the dam portion is inserted through the grooved portion when the fitting portion is fitted into the connection member, and the storage portion is covered by the connection member when the fitting portion is fitted into the connection member.

14. The endoscope according to claim 10, wherein the insertion section further comprises a groove portion in the connection member, wherein the dam portion is inserted through the groove portion when the fitting portion is fitted into the connection member, and the storage portion is covered by the connection member when the fitting portion is fitted into the connection member.

15. The endoscope according to claim 11, wherein the insertion section further comprises a groove portion in the connection member, wherein the dam portion is inserted through the groove portion when the fitting portion is fitted into the connection member, and the storage portion is covered by the connection member when the fitting portion is fitted into the connection member.

16. The endoscope according to claim 12, wherein the insertion section further comprises a groove portion in the connection member, wherein the dam portion is inserted through the groove portion when the fitting portion is fitted into the connection member, and the storage portion is covered by the connection member when the fitting portion is fitted into the connection member.

* * * * *